United States Patent [19]
Forberg

[11] Patent Number: 4,895,340
[45] Date of Patent: Jan. 23, 1990

[54] CLAMP FOR ADJUSTING THE THROUGHFLOW CROSS-SECTION OF A TUBE, I N PARTICULAR FOR MEDICAL DEVICES INTENDED FOR ONCE-ONLY USE

[76] Inventor: Hans-Jürgen Forberg, Sebenter Weg 4, D-2432 Damlos, Fed. Rep. of Germany

[21] Appl. No.: 271,174
[22] Filed: Nov. 14, 1988

[30] Foreign Application Priority Data
Nov. 17, 1987 [DE] Fed. Rep. of Germany ....... 3738965

[51] Int. Cl.⁴ ............................................. F16L 55/14
[52] U.S. Cl. ...................................................... 251/6
[58] Field of Search ................................. 251/6, 4, 5, 7

[56] References Cited
U.S. PATENT DOCUMENTS

| | | |
|---|---|---|
| 4,065,093 | 12/1977 | Phillips ..................................... 251/6 |
| 4,270,725 | 6/1981 | Scott et al. ............................... 251/6 |
| 4,475,709 | 10/1984 | Becker ..................................... 251/6 |

*Primary Examiner*—Arnold Rosenthal
*Attorney, Agent, or Firm*—Balogh, Osann, Kramer, Dvorak, Genova & Traub

[57] ABSTRACT

A clamp for adjusting the throughflow cross-section of a tube, in particular for medical devices intended for once-only use, essentially comprises a U-shaped elongted clamp housing and a clamping roller longitudinally displaceable in the housing, as well as a clamping area angularly positioned with respect to the housing cross-piece, narrowing in the longitudinal direction of the housing and intended to establish the required throughflow cross-section of the tube. To prevent readjustment of a throughflow cross-section once this has been set, provision is made for the clamping area forming the throughflow cross-section of the tube to be formed by means of an annular notch at one edge of the clamping roller in conjunction with a housing sidewall, whilst forming a narrow acute-angled triangular cross-section which supports the tube on all sides.

5 Claims, 2 Drawing Sheets

CLAMP FOR ADJUSTING THE THROUGHFLOW CROSS-SECTION OF A TUBE, I N PARTICULAR FOR MEDICAL DEVICES INTENDED FOR ONCE-ONLY USE

BACKGROUND OF THE INVENTION

The invention relates to a clamp for adjusting the throughflow cross-section of a tube, in particular for medical devices intended for once-only use, comprising a substantially U-shaped elongated clamp housing and a clamping roller longitudinally displaceable in the said housing, a first portion of the tube being adapted to be clamped between the cross-piece of the housing and the peripheral surface of the clamping roller, as well as a clamping area arranged angularly with respect to the crosspiece, narrowing in the longitudinal direction of the housing and intended for adjusting the remaining portion of the tube, which forms the required throughflow cross-section.

The throughflow cross-section of a tube may be narrowed by means of a clamp of this kind, by displacing the clamping roller within the clamp housing and the throughflow quantity of a fluid medium may be adjusted in this manner.

DESCRIPTION OF THE PRIOR ART

A clamp of this nature is disclosed in German Patent Specification No. 22 42 539. The clamp described therein is provided in the housing cross-piece with a channel-like recess, which tapers in width and, has a depth such that the flexible tube may be freely inserted by angular deflection into the corresponding cross-sectional part of the recess, whereby the corresponding throughflow cross-section is set up.

Another clamp for a tube comprising an elongated U-shaped base element is disclosed in German Patent Specification No. 27 18 985, the cross-piece of the element being constructed as a plane clamping surface and its sidewalls having provided in them a fixedly installed semi-circular clamping plate with an operating lever, the thickness of which, corresponds to the spacing of the sidewalls. The clamping plate has an opening of constant radial depth over a quarter of the circular circumference, whilst having a constantly diminishing width, so that the tube incurs an L-shaped deformation.

A medical clamp is also described in German Patent Specification No. 20 43 551, which comprises an elongated U-shaped housing, and a clamping roller guidedly adjustable therein in longitudinal direction, the flexible tube being clamped between the cross-piece of the housing and the periphery of the clamping roller. The housing cross-piece, has formed in it a central groove or notch which tapers in width and into which a part of the tube is forced to establish the throughflow cross-section in question.

In the case of all the known constructions, it has been found in practice that the momentarily set flow cross-section of the tube portion in queston ultimately diminishes further, which is attributed to the assumption that the restoration capability of the flexible tube manifested as a resistance against deformation, as well as its wall thickness, are altered by the so-called cold flow effect caused by the constant stress in the condition set up. The throughflow quantity traversing the tube consequently equally diminishes constantly and may drop to practically nothng in the case of a very small throughflow cross-section, so that a readjustment is required in each case at a particular time following the initial setting and no constant co-ordination is possible between the positions of the clamping roller and the throughflow quantity.

SUMMARY OF THE INVENTION

It is accordingly an object of the invention to provide an improved clamp of the kind referred to in the foregoing, in which, once the throughflow quantity has been adjusted, it is maintained within very close tolerances, so that a readjustment is unnecessary, and wherein the throughflow quantity may be adjusted easily.

This object is achieved by the clamp, in accordance with the invention, in that the longitudinally displaceable clamping roller is provided—for the purpose of forming a clamping area—with a concentric annular notch in its one circumferential edge portion, the annular surfaces of which are all formed as clamping surfaces for the remaining tube portion, that a clamping ridge is provided which is situated axially opposite to the radial clamping surface of the annular notch, is integral with the sidewall of the housing and narrows the throughflow cross-section in the longitudinal direction of the housing, and that the radial clamping surface of the annular notch and/or the clamping surface of the clamping ridge extend inclined with respect to the clamping surface of the housing cross-piece for the purpose of forming a specified clamping triangle.

Consequently, the present invention provides that, once the throughflow quantity has been adjusted, it remains in being within very close tolerances, so that a readjustment of the clamping roller is unnecessary. The flexible tube is clamped omnilaterally in the area of the open cross-section of the clamp, in such manner that a variation of the set throughflow cross-section of the tube is impossible during the subsequent settling of the clamping roller caused by cold flow. The throughflow cross-section set up is equivalent to that of a triangle. In this connection, it has been discovered that there is a relationship between the form of the triangular area and the constancy of the throughflow quantity, once this has been established, inasmuch as the subsequent settling of the clamping roller leads to an increase of the throughflow cross-section with a triangular shape which is too acute, and to a decrease of the same with a triangular shape which is too obtuse. To obtain the optimum cross-sectional shape, provision is thus made according to a preferred feature of the invention to provide the said open cross-section of the clamp with the shape of an at least substantially isosceles triangle, in which connection it has further been discovered to be advantageous for a triangle of this kind to be formed at the edge of the housing cross-piece.

Another preferred embodiment of the invention makes provision for the spacing between the sidewalls of the clamp housing to be smaller than the width of the clamping roller, which has the result that the clamping roller is always kept under slight initial stress by the sidewalls. This has the advantage that the lateral setting of the clamping roller is fixed without play, which is equally advantageous in respect of the constancy of the throughflow cross-section of the tube after performing an adjustment, even during handling. The light initial stress on the sidewalls also prevents lateral deflection of the sidewalls under the clamping force of the clamping roller, which would be equivalent to an enlargement of the open cross-section.

Further objects and advantageous features of the invention will become apparent from the following detailed description taken in conjunction with the accompanying drawings which illustrate a preferred embodiment thereof.

DETAILED DESCRIPTION OF THE PREFERRED EMBODIMENT

Figure 1:
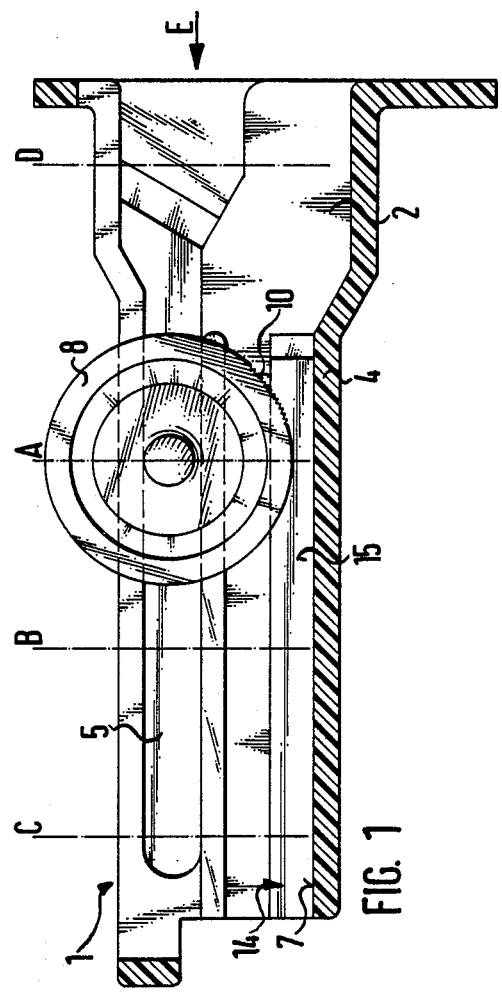
FIG. 1 shows a sideview of a clamp in accordance with a preferred embodiment of the invention, in longitudinal cross-section, without a tube.

According to FIG. 1, the clamp comprises a U-shaped plastics material clamp housing 1, having two sidewalls 2 and 3 as well as a cross-piece 4, which is preferably produced by an injection molding process. The sidewalls 2 and 3 have molded into them guideways 5 extending parallel to the cross-piece 4, which widen in tapered fashion and open towards the one end of the clamp housing 1. The inner surface 7 of the cross-piece 4 forms a clamping surface for a flexible tube 6 which, on the other hand, is clamped by means of a clamping roller 8 which in its centre comprises axial pins 9 situated at both ends, which engage in the guideways 5. The peripheral surface 10 of the clamping roller 8 is arranged to provide grip, for example by knurling, and faces the clamping surface 7 with a spacing therebetween which is a little smaller than twice the wall thickness of the flexible tube 6. According to FIGS. 2,3 nd 4, a first portion of the tube is clamped between the peripheral surface 10 of the clamping roller 8 and the clamping surface 7 of the housing cross-piece 4.

At its circumferential corner section, the clamping roller 8 has a concentric annular notch 11 comprising a radial clamping surface 12 and a circumferential clamping surface 13. The radial clamping surface 12 is preferably made in a tapering undercut form so that it extends with a slope with respect to the clamping surface 7 of the cross-piece 4. The radial clamping surface 12 of the annular notch 11 is axially confronted by a clamping ridge 14 which is integral with the housing sidewall 2 and forms another clamping surface 15 which in the illustrated example extends at right angles to the clamping surface 7 of the housing cross-piece 4 and also merges in rounded form into the clamping surface 7. Moreover, the clamping ridge 14 is so formed that its clamping surface 15 extends convergently with respect to the other sidewall 3 of the housing 1 and in the longitudinal direction of the latter and has approximately the same height as the clamping surface 12, so that on displacement of the clamping roller 8, a constantly diminishing cross-section is present between the surfaces 12,13 and 14 in conjunction with the clamping surfaces 12 and 13 of the annular notch 11. This cross-section has a triangular shape, into which the remaining portion of the tube is forced whilst forming a triangular throughflow cross-section, the rate of throughflow set depending on the axial position of the clamping roller 8 in each case.

Figure 6:
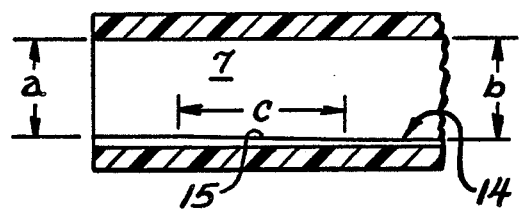
FIG. 6 is a partial cross-section through the clamp along the line 6—6 in FIG. 1.

As shown in FIG. 6, the width b between the inner surface of the sidewall 3 and the clamping surface 15 on the clamping ridge 14 on the sidewall 2 converges along the distance c up to the end of the sidewalls 2 and 3 to reach a width a which is smaller than the width b. As a result of the foregoing construction, the side of the roller 8 continues to press harder a portion of the tube 6 against the clamping surface 15 as the roller 8 moves from the position A in FIG. 1 to position C.

Figure 2:
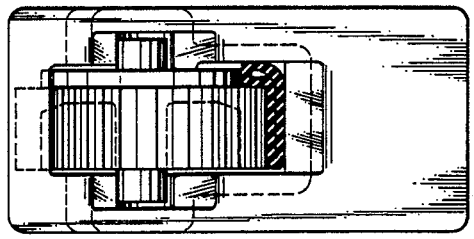
FIG. 2 shows an end view of the clamp in the direction of arrow E in FIG. 1 in the position corresponding to the maximum possible throughflow cross-section of the clamped tube.

In an alternative embodiment, it is also possible for the clamping surface 15 of the clamping ridge 14 to extend at an obtuse angular inclination with respect to the clamping surface 7 of the housing cross-piece 4 and for the radial clamping surface 12 of the annular notch 11 not to be undercut in tapered fashion. This clamping surface 12 may however also be undercut in tapered fashion, as shown in FIGS. 2,3 and 4.

A triangle is formed in each case, whereby the tube portion in question is deformed in triangle form in a specific manner and is also supported trilaterally when the clamping roller 8 is set alongside the clamping ridge 14. As a rule, the tube portion in question at least substantially assumes the shape of an isosceles triangle, which is commonly acute-angled and elongated.

Figure 3:
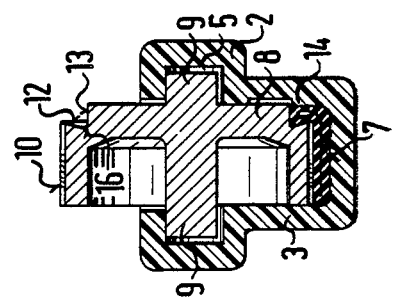
FIG. 3 shows a cross-section through the clamp along the line B—B in FIG. 1.
Figure 4:
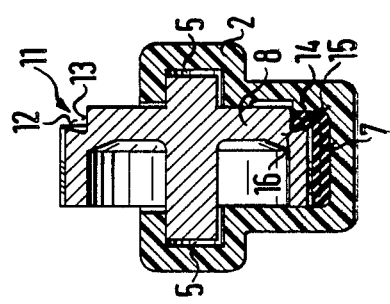
FIG. 4 shows a cross-section through the clamp along the line C—C, in FIG. 1.
Figure 5:
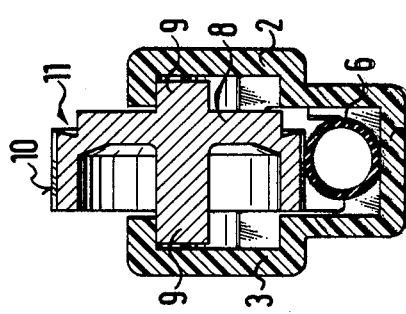
FIG. 5 shows a cross-section through the clamp along the line D—D, in FIG. 1, that is to say with the clamping roller situated in the initial position, in which the tube is not clamped.

The inner edge section 16 of the annular notch 11 is preferably also made in rounded form, as will be apparent from FIGS. 3,4 and 5, to deprive the tube of any possibility of escape in this area too. If desirable, the outer edge of the radial clamping surface 12 of the annular notch 11 may also be made in rounded form.

According to another feature of the invention, the clamping roller 8 may be mounted in a slight retention fit between the sidewalls 3 and 4 of the housing 1, so that the clamping roller may reliably retain its position, once this has been set, without subsequent settling, and the sidewalls thereby acquire a stable position, so that they no longer yield to the pressure of the clamped tube. The point at which the clamping roller 8 bears on the sidewalls 3 and 4 of the housing 1 is illustrated in FIGS. 2,3 and 4.

What is claimed is:

1. A clamp for adjusting the throughflow cross-section of a tube, in particular for medical devices intended for once only use, comprising:

an elongated clamp housing of substantially U-shaped cross-section having side walls and a cross-piece;

a clamping roller having a circumferential surface and being longitudinally displaceable in said housing, whereby a first part of the tube is adapted to be fully clamped between said housing cross-piece and said circumferential surface;

an annular concentric notch having annular surfaces provided in a peripheral corner area of said clamping roller for the purpose of forming a further clamping area, said annular surfaces being formed as clamping surfaces for the remaining tube portion; and a clamping ridge having a clamping surface and being integral with a housing side wall and positioned axially opposite to the radial clamping surface of said annular notch and adapted to narrow the throughflow cross-section of the remaining portion of the tube in the longitudinal direction of the housing, at least one of said radial clamping surfaces of said annular notch and said clamping surface of said clamping ridge extending at an inclination to the clamping surface of said housing cross-piece for the purpose of defining a specific triangular cross-section of said further clamping area.

2. A clamp according to claim 1, wherein the radial clamping surface of said annular notch and the clamping surface of said clamping ridge commonly have an identical height and form the sides of an at least substantially isosceles and preferably acute-angled triangle, whereas the circumferential clamping surface of said annular notch forms the base side of the isosceles clamping triangle.

3. A clamp according to claim 1, wherein the clamping surface of said clamping ridge and the clamping surface of said housing cross-piece coincide in an area which is produced in rounded form.

4. A clamp according to claim 1, wherein the annular notch has an inner corner portion which is produced in rounded form.

5. A clamp according to claim 1, wherein said clamping roller is being held in position by a lightly held fit acting between the side walls of said clamp housing and lateral faces of the roller.

* * * * *